United States Patent [19]

Thurman et al.

[11] Patent Number: 5,484,789
[45] Date of Patent: Jan. 16, 1996

[54] CALCIUM CHANNEL BLOCKERS TO IMPROVE PRESERVATION OF ORGANS STORED FOR TRANSPLANTATION

[75] Inventors: Ronald G. Thurman; John J. Lemasters, both of Chapel Hill, N.C.

[73] Assignee: The University of North Carolina at Chapel Hill, Chapel Hill, N.C.

[21] Appl. No.: 429,288

[22] Filed: Oct. 31, 1989

[51] Int. Cl.$^6$ ................................. A61K 31/435
[52] U.S. Cl. .......................................... 514/277
[58] Field of Search ............................. 514/277

[56] References Cited

PUBLICATIONS

Chem Abst., 110:165854j (1989), Yang et al.
Chem. Abst., 110:107869g (1989), Zhang.
Weishaar et al., "The Beneficial Effect of a Calcium Channel Blocker, Diltiazem, on the Ischemic–Reperfused Heart", Journal of Molecular and Cellular Cardiology (1980), vol. 12, pp. 993–1009.
Belzer et al., "Principles of Solid–Organ Preservation by Cold Storage", Transplantation Overview, vol. 45, No. 4, Apr. 1988, pp. 673–676.
Currin et al., "Carolina Rinse Solution Protects Adenosine Triphosphate–Depleted Hepatocytes Against Lethal Cell Injury", Transplantation Proceedings, vol. 23, Feb. 1991, pp. 645–647.
Caldwell–Kenkel et al., "Selective Loss of Nonparenchymal Cell Vialbiity After Cold Ischemic Storage of Rat Livers", Transplantation, vol. 45, Apr. 1988, pp. 834–837.
Caldwell–Kenkel et al., "Reperfusion Injury to Endothelial Cells Following Cold Ischemic Storage of Rat Livers", Hepatology, vol. 10, (1989), pp. 292–299.
Peck, Robert C. and Lefer Allan M., "Protective effect of nifedipine in the hypoxic perfused cat liver", Agents and Actions, vol. 11, 4 (1981), pp. 421–424.
Thurman et al., "Protection of Liver by Calcium Entry Blockers", Annals of the New York Academy of Sciences, 522 (1988), pp. 757–770.

*Primary Examiner*—Zohreh Fay
*Attorney, Agent, or Firm*—Cushman, Darby & Cushman

[57] ABSTRACT

A composition for storing tissue prior to transplantation is disclosed, wherein the tissue storage composition comprises a calcium channel blocker. Also disclosed is a method of storing tissue, comprising contacting the tissue to be stored with an amount of a calcium channel blocker sufficient to reduce tissue injury during storage under conditions such that viability of the tissue is maintained.

11 Claims, 5 Drawing Sheets

CALCIUM CHANNEL BLOCKERS TO IMPROVE PRESERVATION OF ORGANS STORED FOR TRANSPLANTATION

BACKGROUND OF THE INVENTION

1. Field of the Invention

The present invention relates to a composition for storing tissues prior to transplantation, and a method for storing such tissues. In one embodiment of the invention, the tissues are human tissues.

2. Background Information

In perfused rat livers stored in cold Euro-Collins solution for 24 hours, hepatic parenchymal cells exclude trypan blue; however, nonparenchymal cells lose viability as quickly as 8 hours upon reperfusion (Caldwell-Kenkel et al, Transplantation 1988; 5:834). These data have suggested to the present inventors that viability of parenchymal cells in liver grafts prior to transplantation (e.g., assessed from ATP levels measured chemically or by $^{31}$P NMR (Kamike et al, Transplantation 1988; 45:138) is a poor predictor of surgical outcome. Further, it follows from this reasoning that preservation of nonparenchymal cells is critical for successful liver transplantation.

In perfused livers, the injury to non-parenchymal cells following cold storage involves mainly sinusoidal endothelium (Caldwell-Kenkel et al, Hepatology 1989; 10:292). Further, in an in vivo model of liver transplantation, disturbances in the microcirculation and an injury to about 20% of hepatic parenchymal cells has been observed 24 hours postoperatively. However, it was found that the injury to the hepatic parenchymal cells could be prevented almost entirely by rinsing the organ with nitrogen-saturated buffer. Based on the results of these two models, it was concluded that a reperfusion injury occurs in liver transplantation (Thurman et al, Transplantation 1988; 46:502).

Following cold storage and reperfusion, activation of Kupffer cells was detected based on electron microscopy (Caldwell-Kenkel et al, Hepatology 1988; 8:289), and uptake of colloidal carbon (Thurman et al, The Kupffer Cell Fndn., Rijswijk, The Netherlands, 1989: 159). Further, an inhibitor of Kupffer cell function, methyl palmitate, diminished particle phagocytosis and increased postoperative survival time nearly 3-fold. Kupffer cells produce a number of highly toxic peptides including tumor necrosis factor and platelet activating factor and they release a variety of potent proteases on activation. Calcium is most likely involved in these processes, since prostanoid production by Kupffer cells was increased by the calcium ionophore, A23187 (Dieter et al, Eur. J.Biochem 1988; 255:61).

This suggested to the inventors that a calcium channel blocker would have a good effect on tissues being stored prior to transplantation.

SUMMARY OF THE INVENTION

It is an object of the invention to provide a composition for storing tissues prior to transplantation.

It is another object of the invention to provide a method for storing such tissues.

According to one embodiment, the invention is directed to a tissue storage composition comprising a calcium channel blocker.

According to another embodiment, the invention is directed to a tissue storage method which comprises contacting a tissue to be stored with an amount of a calcium channel blocker sufficient to reduce tissue injury during storage under conditions such that viability of the tissue is maintained.

DETAILED DESCRIPTION OF THE INVENTION

As noted above, the invention relates to a tissue storage composition comprising a calcium channel blocker.

The calcium channel blocker can be of any type, and is most preferably dihydropyridine. Examples of dihydropyridine include nifedipine, nitrendipine, nicardipine, nimodipine, niludipine, riodipine (ryosidine) felodipine, darodipine, isradipine, (+)Bay K 8644, (−)202–791, (+)H 160/ Sl, PN 200-110 and preferably nisoldipine.

Other examples of the calcium channel blocker include benzothiazepine, such as diltiazem (dilzem) and TA 3090 and phenylalkylamine, such as verapamil (isoptin), desmethoxyverapamil, methoxy verapamil (D-600, gallopamil or (−)D-888), prenylamine, fendiline, terodiline, caroverine, perhexiline.

In a tissue storage composition comprising a dihydropyridine-type calcium channel blocker, the dihydropyridine is effective at a concentration of 0.1–10 μM, and preferably 1.4 μM. Other calcium channel blockers such as benzothiazepine or phenylalkylamine-type calcium channel blocker are effective at concentrations of 0.1–50 μM, when used in a tissue storage composition.

In another embodiment, the invention relates to a tissue storage method which comprises contacting a tissue to be stored with an amount of a calcium channel blocker sufficient to reduce tissue injury during storage under conditions such that viability of the tissue is maintained.

Tissues can remain in solution for about 4 hours to 72 hours. The tissues can be stored for varying amounts of time depending on the type of solution used in the tissue storage solution. For example, tissues can be stored for 4 to 8 hours if Euro-Collins solution as defined below in Example 1 is used, or for 8 to 16 hours if University of Wisconsin solution as defined below in Example 1 is used.

Any balanced salt solution can be used, in the tissue storage composition. Additional examples include Ringer's solution, saline solution and 5% dextrose in water.

The tissues are stored at 0°–4° C.

Tissues are defined as any tissues, cells or organs, including liver, lung, kidney, pancreas, heart, gut, small bowel and endocrine organs. In one embodiment, the tissues can be human tissues.

EXAMPLE 1

Hepatoprotective Effect of Nisoldipine

The hepatoprotective effect of nisoldipine using Euro-Collins solution and University of Wisconsin solution and was tested as described below. The composition of the Euro-Collins solution and the University of Wisconsin solution are as follows.

| Euro-Collins Solution | | |
|---|---|---|
| $NaHCO_3$ | 10 mM | 0.84 g/l |
| glucose | 200 mM | 36.03 g/l |
| KCl | 15 mM | 1.12 g/l |
| $K_2HPO_4$ | 43 mM | 7.49 g/l |
| $KH_2PO_4$ | 15 mM | 2.04 g/l |

| University of Wisconsin Solution | |
|---|---|
| Potassium Lactobionate | 100 mM |
| $KH_2PO_4$ | 25 mM |
| $MgSO_4$ | 5 mM |
| Raffinose | 30 mM |
| Adenosine | 5 mM |
| Glutathione | 3 mM |
| Insulin | 100 U/l |
| Penicillin | 400 U/l |
| Dexamethasone | 8 mg/l |
| Allopurinol | 1 mM |
| Hydroxyethyl starch | 50 g/l |

The components in the Euro-Collins solution and the University of Wisconsin solution are dissolved in distilled water.

In the Euro-Collins group, livers were rinsed and stored in Euro-Collins solution alone or Euro-Collins solution containing nisoldipine dissolved in dimethylsulfoxide (DMSO) to a final concentration of 0.4%, and diluted in Euro-Collins solution to desired concentrations. Thereafter, livers were rinsed with 20 ml of cold Ringer's solution and implanted. In the University of Wisconsin group, livers were rinsed and stored for 8 hours or 16 hours in University of Wisconsin solution alone or with nisoldipine. Nisoldipine was dissolved in DMSO and diluted in either Euro-Collins solution or University of Wisconsin solution to a final concentration of 1.4 μM at 4° C., with 4 to 14 livers in each group.

Figure 1:
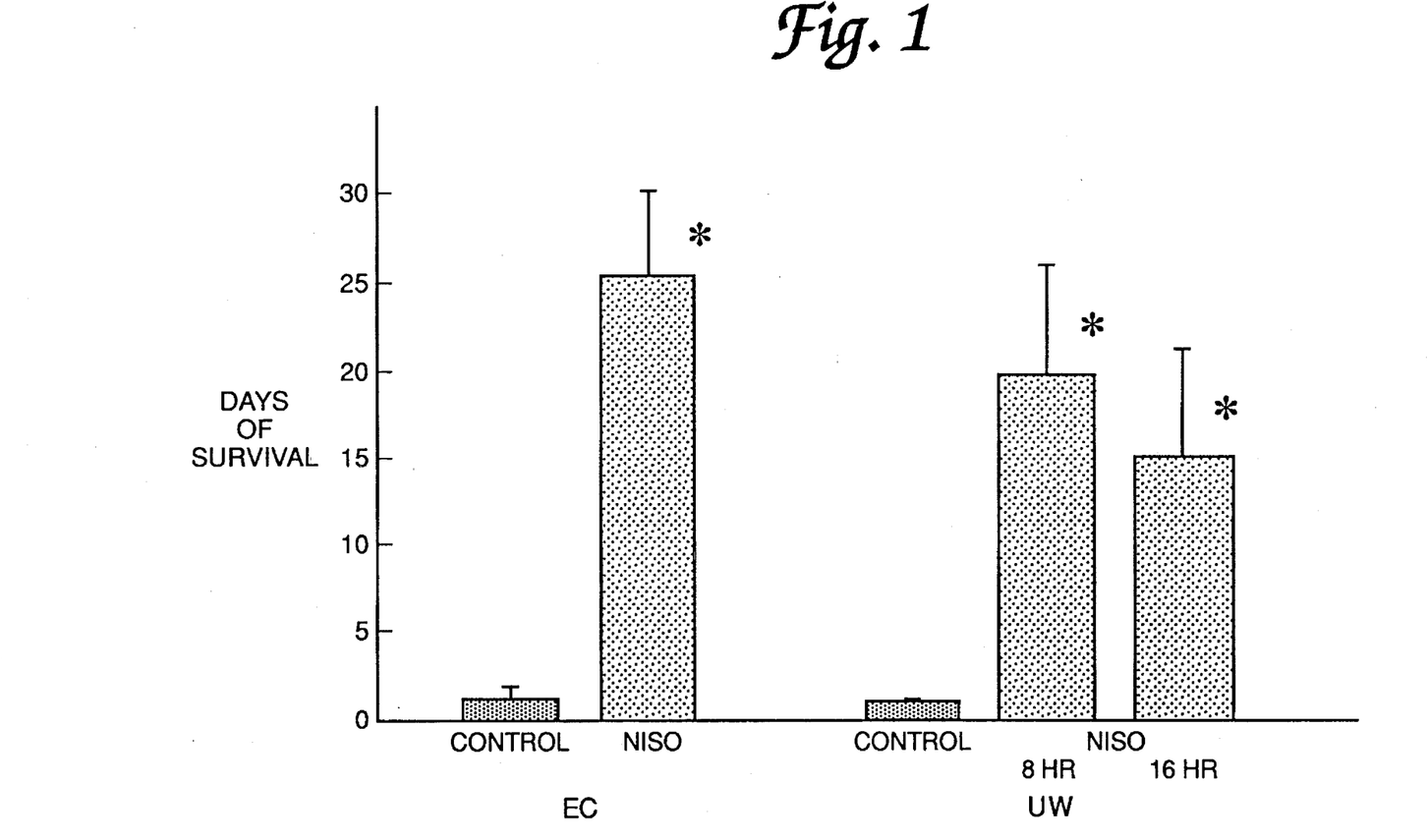
FIG. 1 is a bar graph which shows the effects of nisoldipine on the survival time of livers stored in Euro-Collins or University of Wisconsin cold solution. EC, Euro-Collins, UW, University of Wisconsin solution; CONT, control; NISO, nisoldipine. *, $p<0.05$ for comparison with the appropriate control group; **, $p<0.02$ for comparison with the appropriate control group.

In livers stored for 4 hours in Euro-Collins solution prior to transplantation as described below, postoperative survival time was less than one day (FIG. 1).

On the other hand, if the organ was rinsed and stored in Euro-Collins solution containing nisoldipine, survival time was increased significantly to 25 days by inclusion of the dihydropyridine-type calcium channel blocker, nisoldipine.

In these experiments, the inventors assumed that survival for 30 days was permanent.

Most clinical work today involves storage of livers in the University of Wisconsin cold storage solution; therefore, the effect of nisoldipine on survival in livers stored in University of Wisconsin solution was examined. In the rat, storage of livers for 8 or 16 hours in University of Wisconsin solution also resulted in survival times of less than one day. Nisoldipine increased survival time significantly to 15 to 20 days in livers stored in University of Wisconsin solution as well (FIG. 1).

Figure 2A:
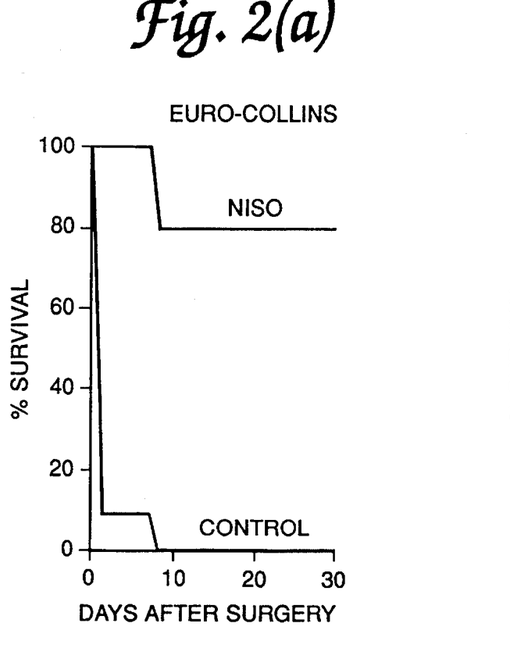
FIG. 2(a) is a graph which shows the effect of nisoldipine on the time course of survival for livers stored in Euro-Collins solution.
Figure 2B:
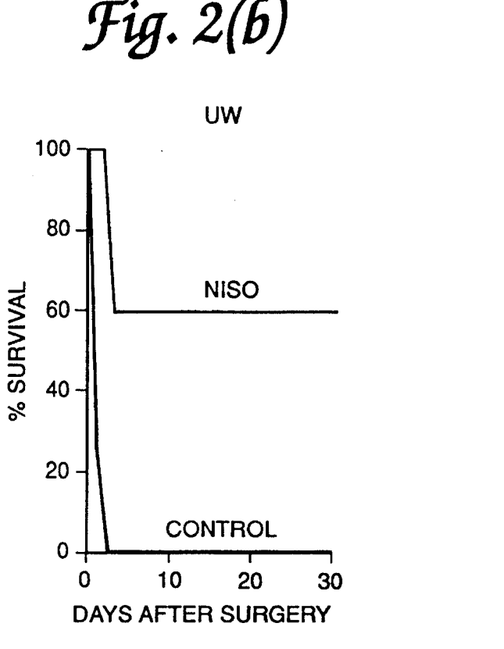
FIG. 2(b) is a graph which shows the effect of nisoldipine on the time course of survival for livers stored in University of Wisconsin solution.

Survival curves following liver transplantation surgery, where the effect of nisoldipine under the same conditions as described above with respect to FIG. 1 are depicted in FIG. 2(a) and 2(b). In control livers stored in Euro-Collins solution for 4 hours, the number of surviving rats declined rapidly and no rat survived beyond 8 days (FIG. 2(a). Nisoldipine alone improved rates to around 80%. Similar results were observed in livers stored in University of Wisconsin solution (FIG. 2(b)). In groups stored for 8 hours in University of Wisconsin solution, all rats died within 3 days, whereas the addition of nisoldipine increased survival rates to about 60%.

Transplantation

Inbred female Lewis rats (female, 175–200 g) were used for all transplantations to exclude immunological interference. Liver transplantations were performed under ether anesthesia and rats were allowed to take food and water ad libitum postoperatively. Sixty-two orthotopic liver transplantations were performed using the technique described by Zimmermann et al (Transplant Proc 1979; 1:571 and Kamada et al (Transplantation 1979; 28(1):47). Briefly, cuffs were placed on the portal vein and subhepatic vena cava of the donor liver and the organs were stored promptly upon removal from an organism, preferably from 15 min. to 60 min. after removal at 0°–4° C. in Ringer's solution for 1 hour, Euro-Collins solution for 4 hours, or University of Wisconsin solution for 8 or 16 hours.

In some experiments, nisoldipine was added to the storage solution. During explantation, the organ was rinsed with about 20 ml of this solution.

Thereafter, livers were transplanted by connecting the suprahepatic vena cava with a running suture, inserting the cuffs into the appropriate vessels and anastomosing the bile duct over an intraluminal polyethylene splint. Implantation surgery required less than 50 minutes during which time the portal vein was clamped for 17 to 25 minutes. Survival was defined when rats were alive 30 days following transplantation surgery. Ten out of 10 rats transplanted with the livers stored one hour in Ringer's solution survived for 30 days, confirming the validity of this technique.

EXAMPLE 2

Hepatoprotective Effect of Nisoldipine

Figure 3:
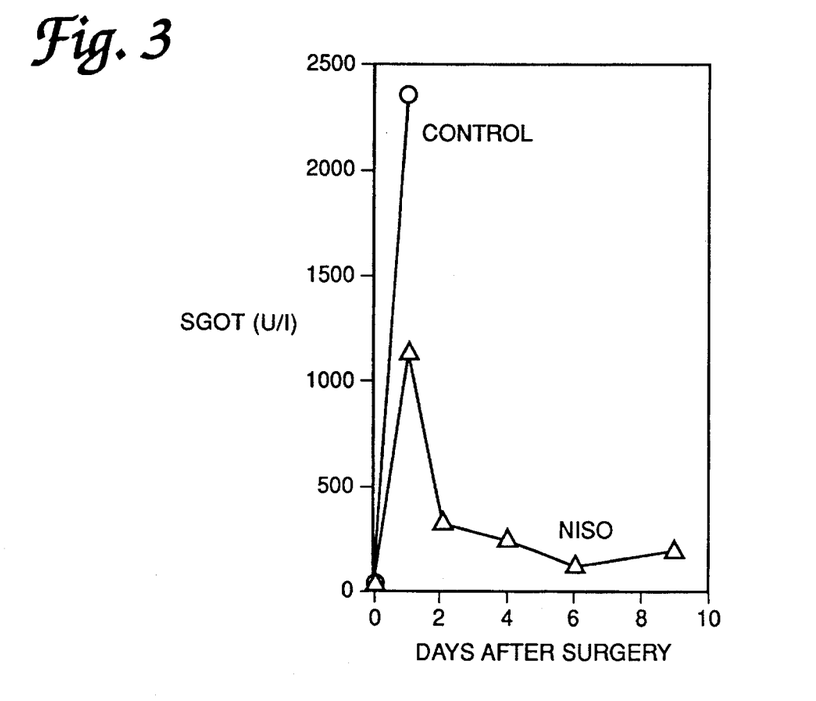
FIG. 3 is a graph which illustrates the serum GOT levels in recipient rats following surgery. Each point represents group means. n=5 to 8 per group.

Liver injury was assessed in these experiments from the release of transaminases (FIG. 3) and histological examinations (FIG. 4) as described below. Following 4 hours of storage in Euro-Collins solution, all rats died within 24 hours and had Serum aspartate amino transferase (SGOT) activity levels greater than 2000 U/l just prior to death. In all treatment groups, SGOT also reached maximal values about 24 hours following the operation and then declined toward baseline values for the next 3–4 days. On the other hand, values only reached about 1100–1200 U/l in livers stored in nisoldipine (FIG. 3). In livers stored for 8 hours in University of Wisconsin solution, serum GOT also rose rapidly after the operation to values to around 1800 U/l (data not shown). In the presence of niisoldipine, values only reached around 1000 U/l. Values also subsequently declined towards baseline over the next 5 days postoperatively where they remained at around 100 U/l for up to 30 days.

Figure 4:
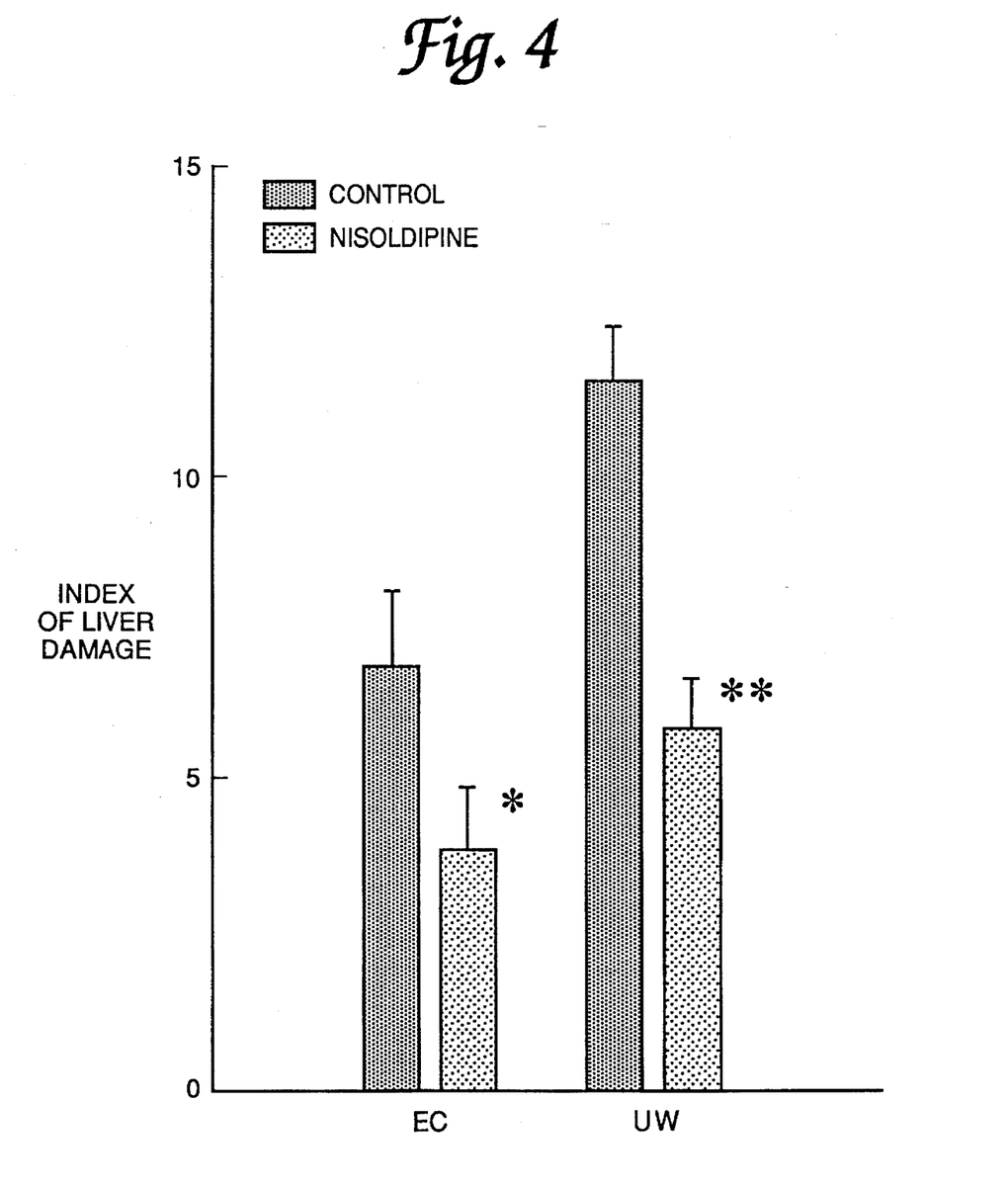
FIG. 4 is a bar graph which shows the effects of nisoldipine on postoperative damage to the liver. Maximal score = 17. Mean + SEM for 5 livers in each group. *, $p<0.05$ compared to the control. **, $p<0.01$ compared to the control.

Livers were examined histologically 48 hours postoperatively because serum enzyme levels (e.g., liver damage) were very high at that time. Liver damage was assessed from a histological score from 0 to 5 based on the degree of necrosis and from 0 to 2 based on six structural parameters: cellular swelling, acidophilic nuclear inclusions, nuclear pyknosis, cellular deposition, cytoplasmic vacuolization, and sinusoidal dilatation. In control livers stored under nonsurvival conditions, the liver damage index was around 7 and 11 in livers stored in Euro-Collins and University of Wisconsin solution, respectively. In the Livers stored with nisoldipine, however, the index was reduced significantly by about 50% in both groups (FIG. 4).

The effect of nisoldipine on the detailed structure of the liver was examined by electron microscopy as described below. In control livers stored for 4 hours and examined 2 hours postoperatively, parenchymal cells were shrunken and bile canaliculi were torn and difficult to identify. Fenestrations of sinus endothelial cells were larger than normal, and some tearing was observed. Kupffer cells were moderately activated as assessed from lamapoeldia formation. On the other hand, if nisoldipine was included in the storage solution, parenchymal cells were not swollen and the endothelium was continuous and intact exhibiting both small and large size fenestrations, which is normal. Under these conditions, Kupffer cells appeared less activated.

Figure 5:
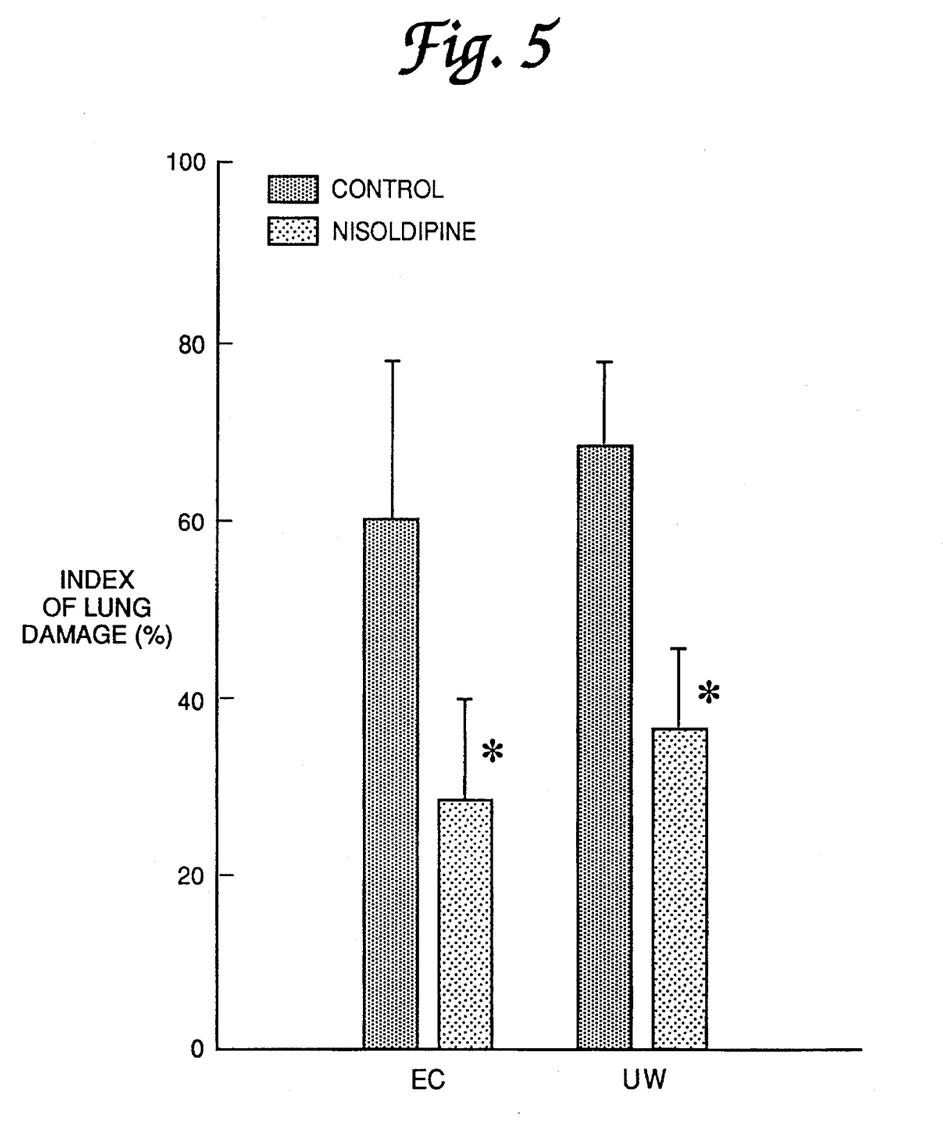
FIG. 5 is a bar graph which shows the effects of nisoldipine on postoperative damage to the lung. The degree of damage to the lung is depicted as a percentage of the damaged area. Mean ± SEM for 5 lungs in each group.

In the lungs of these examined 48 hours postoperatively animals had massive infiltration (60 to 70%) of inflammatory cells associated with massive bleeding was observed in the control, non-survival groups (FIG. 5). In the nisoldipine groups, however, infiltration was reduced significantly by 30 to 50% in both the Euro-Collins and University of Wisconsin groups and bleeding was not observed (FIG. 5). Whether or not this respiratory distress is involved in poor survival or not is presently unknown; however, release of mediators from Kupffer cell or damaged endothelial and parenchymal cells could contribute to this phenomenon.

Clinical Chemistry

Blood samples were collected via the tail vein at one to three day intervals postoperatively. Sera were separated by centrifugation and were kept at −20° C. until enzyme measurements were taken. Serum aspartate aminotransferase (SGOT) activity was measured by standard enzymatic procedures (Bergmeyer, Methods of Enzymatic Analysis, N.Y., Academic Press, 1988).

Histology and Electron Microscopy

Rats were sacrificed 48 hours postoperatively and liver and lung were fixed by perfusion with 2% paraformaldehyde: 2% glutaraldehyde in Krebs-Henseleit buffer, embedded in paraffin, and processed for light microscopy. Sections were stained with hematoxylin and eosin.

For scanning electron microscopy, livers fixed as described above were cut into 1-cm cubes and placed overnight in cold secondary fixative containing 2% glutaraldehyde in 0.1M sodium phosphate buffer, pH 7.4. The tissue was washed subsequently in water, dehydrated in 2,2-dimethoxypropane, and critical point dried in carbon dioxide. The dried tissue was cut manually with a razor blade, mounted on an aluminum stub, and coated with gold-palladium using a sputter evaporator, and viewed in a JEOL 820 scanning electron microscope (Lemasters et al, J. Cell Biol. 1983; 97:778).

EXAMPLE 3

Inhibition of Particle Phagocytosis of Kupffer Cells by Nisoldipine

Figure 6:
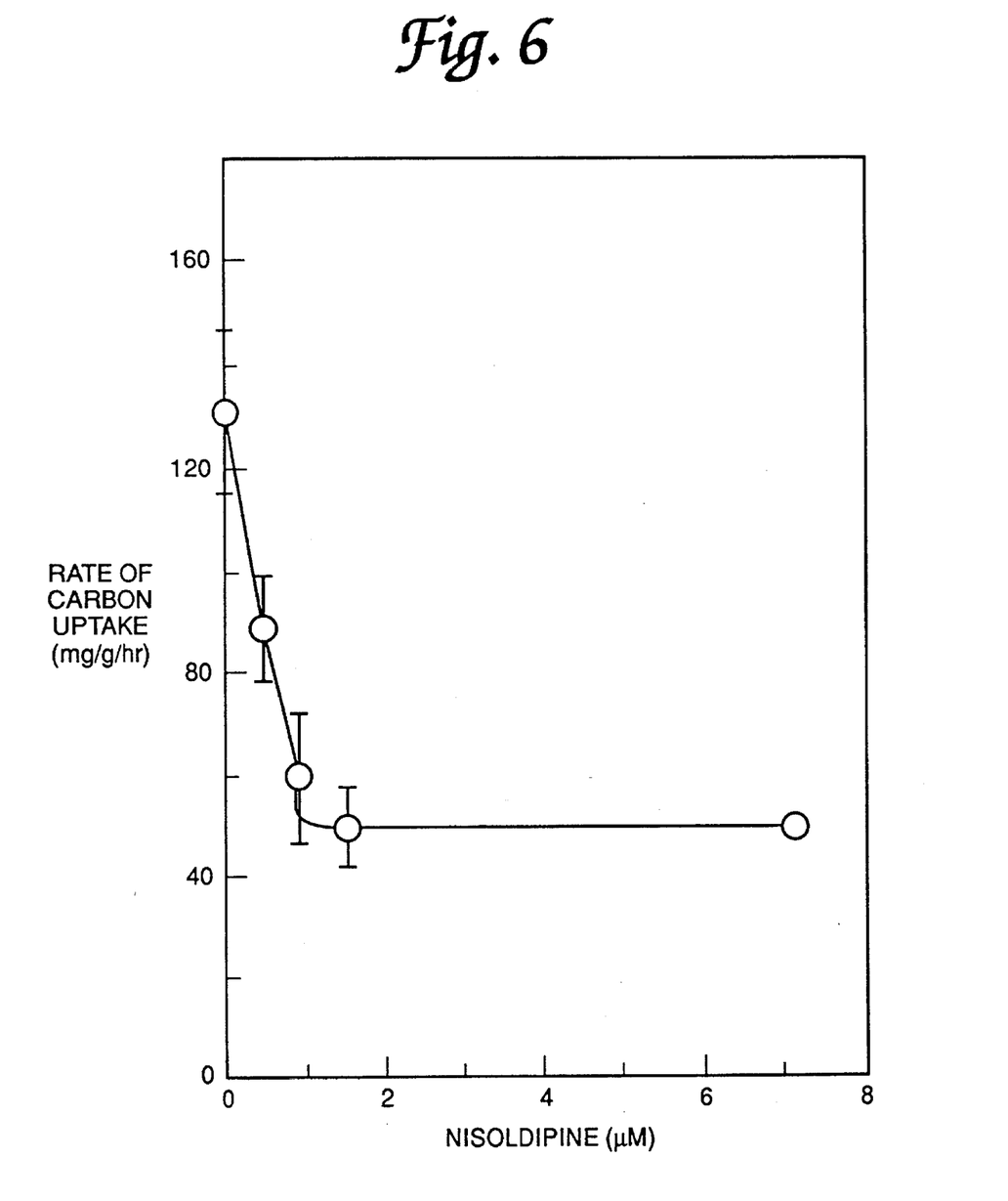
FIG. 6 is a graph which shows the effects of nisoldipine on the rate of carbon uptake in perfused liver. Mean ± SEM n=4 livers per group.

To determine if nisoldipine acted on Kupffer cells, a new method to monitor particle phagocytosis based on uptake of colloidal carbon by the isolated, perfused liver was employed (Thurman et al, The Kupffer Cell Fndn., Rijswijk, The Netherlands, 1989:159) as described below. In livers stored for 4 hours in Euro-Collins solution under non-survival conditions, rates of carbon uptake in livers subsequently perfused were around 130 mg/g/h (FIG. 6). If nisoldipine was included in the storage media a dose-dependent decrease in carbon uptake in the perfused liver was observed. Rates were reduced maximally to values around 50 mg/g/h with 1.4 µM nisoldipine; half-maximal inhibition was observed with about 0.4 µM (FIG. 6).

Uptake of Colloidal Carbon

A suspension of colloidal carbon was prepared by dialyzing 10–15 ml of India Ink (Pellican black #17) against distilled water for 48 hours utilizing a Spectrapor semipermeable membrane with a 12,000–14,000 molecular weight exclusion cutoff (Spectrum Medical Industries, Los Angeles). The suspension was stored at refrigerator temperatures for up to 30 days before use and was diluted to a concentration of 2 mg/ml prior to use. Livers were stored in Euro-Collins solution with or without nisoldipine at a concentration of 1.4 µM at 4° C. for 4 hours. Subsequently, livers were perfused for 20 to 40 min with Krebs-Henseleit buffer (pH 7.4, 37° C.), saturated with 95% $O_2$:5% $CO_2$ in a hemoglobin-free, nonrecirculating system as described previously (Scholz et al, Eur. J. Biochem. 1973; 38:64). Carbon was infused (2 mg/ml), and the absorbance of carbon was monitored continuously at 623 nm and rates of carbon uptake were calculated from influent minus effluent concentration differences, the flow rate, and the liver wet weight (Thurman et al, The Kupffer Cell Fndn., Rijswijk, The Netherlands, 1989: 159).

Results: Potential Clinical Usefulness of Calcium Channel Blocker

The most dramatic finding in these experiments was the nearly complete conversion of non-surviving into surviving grafts by inclusion of a calcium channel blocker nisoldipine, in the storage solution (FIG. 1). Survival time was increased dramatically in livers stored in either Euro-Collins or University of Wisconsin solution by nisoldipine. Further, survival time was extended nearly 10 fold in liver stored in the University of Wisconsin solution containing 1.4 µM nisoldipine. Inclusion of nisoldipine in the cold-storage media also reduced serum enzyme release from hepatocytes and diminished cell damage and alternations in the hepatic architecture due to cold-storage and reperfusion dramatically by about 50%. In spite of the development of new cold storage solutions (e.g., University of Wisconsin solution), the length of time an organ can be successfully stored is still a major problem in liver transplantation (Starzl et al, Hepatology 1982; 2:614). The results of these experiments demonstrate clearly that survival time can be prolonged dramatically by nisoldipine. Thus, the inventors conclude that surgical outcomes would be influenced positively by inclusion of nisoldipine in cold storage solutions in the clinic.

One could argue that it might not be wise to use calcium channel blockers which have known effects on the hemodynamic system following such a large surgical trauma as liver transplantation. However, the μM concentrations of nisoldipine present in the cold storage solution would be diluted at least to values around 0.6 μg/100 g body weight simply based on the ratio of the liver to body weight. Dihydropyridine-type calcium channel blocker administered in doses of 0.9 μg/100 g body weight did not alter blood pressure (Hberle et al, J. Cardiovasc Pharmacol 1987; 9:S17). Thus, used at concentrations employed in this study, nisoldipine should have minimal effects on the hemodynamic system.

Mechanism of Action of Nisoldipine

In other tissues, dihydropyridine-type calcium channel blockers act primarily on L-type, voltage-activated calcium channels (Lazdunski et al, New York Academy of Sciences, New York, 1988: 131, Seagar et al, New York Academy of Sciences, New York, 1988: 162, Battani et al, New York Academy of Sciences, New York, 1988: 187). However, voltage-dependent calcium channels have yet to be detected in liver, and dihydropyridine binding in hepatic tissue is very weak (Triggle et al, Nitrendipine, Urban & Schwarzenberg, Baltimore, Md., 1984: 33). On the other hand, relatively high (10–40 μM) concentrations of nifedipine and nitrendipine reduced hypoxic injury in the liver (Thurman et al, J. Cardiovas. Pharmacol. 1988; Suppl. 4:257 and Peck et al, Agents Actions 1981; 11:421). These observations, along with the results from these experiments, lead the inventors to hypothesize that calcium is involved in the mechanism of graft failure, and that nisoldipine interferes with this mechanism. Below the inventors examine the possibilities that parenchymal, endothelial or Kupffer cells are primarily sites of action of nisoldipine.

Effect of Nisoldipine on Parenchymal Cells

Parenchymal cells are clearly damaged following transplantation surgery. Even in livers stored under survival conditions, nearly 20% of parenchymal cells were destroyed 24 hours postoperatively (Thurman et al, Transplantation 1988; 46:502). This injury was attributed to an oxygen dependent reperfusion effect, since damage could be reduced dramatically by rinsing the organ with nitrogen-saturated buffer prior to implantation. Under these conditions, a calcium channel blocker reduced cell injury even further (Marzi et al, Forum 1988; 105:371). Moreover, in livers stored under non-survival conditions, massive injury to parenchymal cells was detected in vivo within 2 hours postoperatively by video microscopy. Thus, parenchymal cells are clearly damaged postoperatively, and nisoldipine could act on them directly.

A rich literature exists suggesting that an early event in cell death is a rise in cytosolic calcium (Schanne et al, Science 1979; 206:700). This occurs with hypoxia as well as with a variety of toxic chemicals. Thus, nisoldipine may act directly to prevent this mechanism from occurring. In one study with isolated hepatocytes, LDH release was diminished markedly by a variety of calcium channel blockers including nifedipine (Umeshita et al, Transplant Proc 1989; 21:1290). On the other hand, nitrendipine failed to reduce damage due to chemical hypoxia in isolated hepatocytes. Studies with dihydropyridine-type calcium blockers and hepatocytes are punctuated by the relatively high concentrations (10–30 μM) required for efficacy. Since nisoldipine concentrations during reperfusion should be less than 1 μM, when injury to parenchymal cells occurs, the inventors conclude that the parenchymal cell is an unlikely site of action for the drug. This argument is supported by the observation that cold storage and reperfusion has little effect on parenchymal cells in perfused liver.

Effect of Nisoldipine on Kupffer Cells

When activated, Kupffer cells release a wide variety of toxic peptides including tumor necrosis factor, interleukins, cytokines, prostanoids, platelet activating factor, toxic radicals and proteases (Nolan et al, Hepatology 1981; 1:458). One possibility is that the calcium channel blocker interferes with the activation of Kupffer cells which has been shown to be activated by the calcium ionophore, A23187 (Dieter et al, Eur. J. Biochem 1988:255). Thus, one working hypothesis is that graft failure involves these toxicants.

Evidence in support of the involvement of Kupffer cells in graft failure and in injury to livers perfused after storage has also been presented. First, following cold storage of livers for 24 hours in Euro-Collins solution, uptake of carbon particles by Kupffer cells was nearly doubled upon reperfusion (Thurman et al, Hepatology 1988; 8:1824 (Abstract)) and Kupffer cells were activated morphologically (Caldwell-Kenkel et al, Hepatology 1988; 8:289). Furthermore, treatment of rats with an inhibitor of Kupffer cell function, methyl palmitate, increased survival time significantly from less than one to more than 3 days most likely by acting on Kupffer cells. Thus, evidence in support of the idea that Kupffer cells are involved in the mechanism of graft failure is compelling.

The involvement of proteases in the mechanism of graft failure was suggested by the observation that the liver was limp and flaccid following 24 hours of storage in Euro-Collins solution. Indeed, release of proteases from Kupffer cells is most likely involved in the mechanism of graft failure since a cocktail of protease inhibitors increased survival in the transplantation model significantly. However, protease inhibitors only increased survival time to 11.5 days whereas nisoldipine alone increased survival significantly more to 25 days. Thus, it is possible that nisoldipine prevents release of proteases and the toxicants from Kupffer cells accounting for the relative improvement compared to inhibition of proteases already released. The improvement of calcium and Kupffer cells in the mechanism of graft failure is supported strongly by the observation that nisoldipine diminished particle phagocytosis due to Kupffer cells in the perfused liver in a dose-dependent manner and in a submicromolar concentration range which prevented graft failure in the transplantation mode (FIG. 6).

Effects of Nisoldipine on Endothelial Cells and Microcirculation

Endothelial cells were shown to be particularly vulnerable to reperfusion injury in a model involving liver perfusion following cold storage (Caldwell-Kenkel et al, Transplantation 1988; 5:834). Moreover, endothelium and smooth muscle cells in other tissues exhibit ω-conotoxin and dihydropyridine binding to L-type calcium channels (Rubanyi et al, New York Academy of Sciences, New York, 1988: 226). Thus, endothelial cells may be a primary target for calcium channel blockers in addition to Kupffer cells. Following cold storage, the hepatic microcirculation is disturbed most likely due to collapse of the sinusoids due to contracture of the endothelium due to calcium. The inventors hypothesize that nisoldipine blocks calcium channels in endothelial cells thereby preventing alterations in the microcirculation. In support of this hypothesis, Chazouillres et al (Hepatology 1989; 9:824) demonstrated that vasodilators diminished cell injury following cold storage in vitro. Further, the inventors observed that organs obtained a deep red color due to distribution of hemoglobin in the microcirculation much more quickly in the presence (1 min) than in the absence (3 min) of nisoldipine on completion of surgery. Further, red cells were trapped in the sinusoids of livers stored under non-survival condition; however, this phenomenon was not observed if nisoldipine was included in the storage solution. Since the concentration of nisoldipine employed to alter microcirculation and increase survival time was similar (i.e., 1.4 µM), the inventors concluded that endothelial cells and microcirculation are involved in the mechanism of early graft failure following transplantation.

In these experiments, the concentration of nisoldipine which increased survival time was shown to be effective at the level of Kupffer cells and the microcirculation. Which of these events is primary, and are they in any way interrelated. One hypothesis is that an early event in graft failure postoperatively results in the activation of Kupffer cells. This leads to the release of proteases and damage to the endothelium. In turn, disturbances in the microcirculation occur which ultimately cause focal hypoxia and hepatocellular death. Nisoldipine interferes with the process at the level of the Kupffer and/or endothelial cell and prevents the cascade of events leading to graft failure. Identification of the precise site of action of calcium channel blockers in transplantation is an important area for future research.

While the present invention has been illustrated by detailed descriptions of preferred embodiments thereof, it will be obvious to those skilled in the art that various changes in form and detail can be made therein without departing from the true scope of the invention. For that reason, the invention must be measured by the claims appended hereto.

What is claimed:

1. A composition for the temporary cold storage of living tissue for subsequent use as a transplant comprising aneffective amount of a calcium channel blocker sufficient to reduce tissue injury during storage, wherein said calcium channel blocker is a dihydropyridine derivative.

2. The composition according to claim 1, wherein said dihydropyridine derivative is nisoldipine.

3. The composition according to claim 1, wherein said composition contains 0.1–10 µM of said dihydropyridine derivative.

4. The composition according to claim 3, wherein said composition contains 1.4 µM of said dihydropyridine derivative.

5. A method for the temporary cold storage of living tissue for subsequent use as a transplant which comprises contacting a tissue to be stored with an amount of a calcium channel blocker to reduce tissue injury during storage under conditions such that viability of said tissue is maintained, wherein said calcium channel blocker is a dihydropyridine derivative.

6. The method according to claim 5, wherein said dihydropyridine derivative is nisoldipine.

7. The method according to claim 5, wherein said tissue is stored in said composition from 4 to 72 hours.

8. The method according to claim 5, wherein said tissue is stored in said composition at a temperature in the range of 0°–4° C.

9. The method according to claim 5, wherein said tissue is a human tissue.

10. The method according to claim 5, wherein said tissue is liver tissue.

11. The method according to claim 5, wherein said tissue is lung tissue.

* * * * *